(12) United States Patent
Ouyang

(10) Patent No.: US 11,450,426 B2
(45) Date of Patent: Sep. 20, 2022

(54) TOOTH VIRTUAL EDITING METHOD AND SYSTEM, COMPUTER DEVICE, AND STORAGE MEDIUM

(71) Applicant: BEIJING KEEYOO TECHNOLOGIES CO., LTD., Beijing (CN)

(72) Inventor: Congxing Ouyang, Beijing (CN)

(73) Assignee: BEIJING KEEYOO TECHNOLOGIES CO., LTD., Beijing (CN)

( * ) Notice: Subject to any disclaimer, the term of this patent is extended or adjusted under 35 U.S.C. 154(b) by 34 days.

(21) Appl. No.: 17/054,068

(22) PCT Filed: May 30, 2019

(86) PCT No.: PCT/CN2019/089304
§ 371 (c)(1),
(2) Date: Nov. 9, 2020

(87) PCT Pub. No.: WO2020/073669
PCT Pub. Date: Apr. 16, 2020

(65) Prior Publication Data
US 2021/0241885 A1    Aug. 5, 2021

(30) Foreign Application Priority Data
Oct. 10, 2018    (CN) .......................... 201811178300.3

(51) Int. Cl.
*G16H 30/40*    (2018.01)
*G06T 7/62*    (2017.01)
*G16H 50/20*    (2018.01)

(52) U.S. Cl.
CPC .............. *G16H 30/40* (2018.01); *G06T 7/62* (2017.01); *G16H 50/20* (2018.01); *G06T 2207/10028* (2013.01); *G06T 2207/30036* (2013.01)

(58) Field of Classification Search
CPC ........ G16H 30/40; G16H 50/20; G16H 20/40; G16H 40/67; G16H 50/50; G16H 80/00;
(Continued)

(56) References Cited

U.S. PATENT DOCUMENTS 6,448,640 B2    9/2002    Corisis
6,648,640 B2 *  11/2003   Rubbert ................. G16H 50/50
                                                    433/24
(Continued)

FOREIGN PATENT DOCUMENTS

CN    106562800        *    4/2017   ............... A61B 6/03
CN    106562800 A         4/2017
(Continued)

OTHER PUBLICATIONS

International Search Report corresponding to PCT Application No. PCT/CN2019/089304 dated Jul. 29, 2019. (pp. 4).
(Continued)

*Primary Examiner* — Amara Abdi
(74) *Attorney, Agent, or Firm* — Muncy, Geissler, Olds & Lowe, P.C.

(57) ABSTRACT

A tooth virtual editing method comprises: constructing a three-dimensional image basic database of a human oral cavity; acquiring three-dimensional image data of a user oral cavity, performing image pattern recognition on the three-dimensional image data according to the stored three-dimensional image basic database, recognizing an object to which the image data belongs, and establishing an object annotation system of the user oral cavity, wherein the object
(Continued)

--- constructing a three-dimensional image basic database of a human oral cavity — S1 acquiring three-dimensional image data of a user oral cavity, perform image recognition on the three-dimensional image data according to the stored three-dimensional image basic database, recognizing an object to which the image data belongs, and establishing an object annotation system of the user oral cavity — S2 performing editing on the object according to the object annotation system of the current user, and display an updated three-dimensional image of the teeth — S3 contains a block and/or an entity; and performing virtual editing on the object according to the established object annotation system of the current user, and displaying an updated three-dimensional image of the teeth.

17 Claims, 3 Drawing Sheets

(58) Field of Classification Search
CPC .............. G06T 7/62; G06T 2207/10028; G06T 2207/30036; G06T 2219/004; G06T 2219/2016; G06T 2219/2021; G06T 19/20; G06T 17/00; G06V 20/20; G06V 2201/033; G06V 20/64
See application file for complete search history.

(56) References Cited

U.S. PATENT DOCUMENTS

| | | | |
|---|---|---|---|
| 2003/0027098 A1 | 2/2003 | Manemann et al. | |
| 2004/0205600 A1* | 10/2004 | Kakuta | G06F 40/166 715/205 |
| 2009/0132455 A1 | 5/2009 | Kuo et al. | |
| 2012/0095732 A1 | 4/2012 | Fisker et al. | |
| 2012/0244488 A1 | 9/2012 | Chishti et al. | |
| 2013/0162637 A1* | 6/2013 | Son | G03H 1/08 345/419 |
| 2013/0282351 A1* | 10/2013 | Tank | G06F 30/20 703/11 |
| 2014/0267393 A1* | 9/2014 | Mitchell | G06T 11/60 345/632 |
| 2015/0003726 A1* | 1/2015 | Barker | G06K 9/6262 382/159 |
| 2017/0035536 A1 | 2/2017 | Alvarez Garcia et al. | |
| 2018/0028065 A1* | 2/2018 | Elbaz | G06T 15/08 |
| 2018/0357766 A1* | 12/2018 | Van Der Poel | A61B 5/0062 |
| 2019/0015177 A1* | 1/2019 | Elazar | G16H 30/40 |
| 2020/0184723 A1 | 6/2020 | Ouyang | |

FOREIGN PATENT DOCUMENTS

| | | | |
|---|---|---|---|
| CN | 107252356 | * 10/2017 | ............. A61C 7/002 |
| CN | 107252356 A | 10/2017 | |
| CN | 107240343 A | 1/2018 | |
| CN | 107644454 A | 1/2018 | |
| CN | 107863149 A | 3/2018 | |
| CN | 108062792 A | 5/2018 | |
| CN | 109166625 A | 1/2019 | |
| JP | 2012513787 A1 | 6/2012 | |
| WO | 2017039563 A1 | 6/2017 | |
| WO | 2017218040 A1 | 12/2017 | |

OTHER PUBLICATIONS

Non-Final Office Action corresponding Taiwanese application TW108119236 dated Dec. 16, 2019. (pp. 20).
Final Office Action corresponding Taiwanese application TW108119236 dated Jun. 5, 2020. (pp. 6).
First Office Action of Chinese Patent Application No. 201811178300.3 dated Apr. 14, 2021.
Second Office Action of Chinese Patent Application No. 201811178300.3 dated Aug. 24, 2021.
Third Office Action of Chinese Patent Application No. 201811178300.3 dated Nov. 18, 2021.
Examination Report No. 1 of Australian Patent Application No. 2019358161 dated Oct. 19, 2021.
Examination Report No. 2 of Australian Patent Application No. 2019358161 dated Feb. 28, 2022.
Non-Final Notice of Reasons for Refusal of Japanese Patent Application No. 2020-566292 dated Jan. 25, 2022.
Extended Search Report of European Patent Application 19871231.7 dated Jan. 5, 2022.

* cited by examiner

TOOTH VIRTUAL EDITING METHOD AND SYSTEM, COMPUTER DEVICE, AND STORAGE MEDIUM

The present application claims priority to Chinese Patent Application No. 201811178300.3, entitled "Tooth Virtual Editing Method and System", filed in the Chinese Patent Office on Oct. 10, 2018, the entire contents of which are incorporated herein by reference.

TECHNICAL FIELD

The present application relates to a tooth virtual editing method and system, a computer device and a storage medium.

BACKGROUND

At present, there is a problem existing in the field of oral health globally, i.e. the incidence rate is high while the consultation rate is low.

One reason is that many parts of the oral cavity (such as the posterior molars and the lingual and palatal sides of the dentition) are inconvenient for people to see, and people usually cannot see pathological precursors in the oral cavity, and would not actively make an appointment with the doctor until they experience symptoms such as pain. However, when pain occurs in the oral cavity, people may have got oral diseases such as dental caries, pulpitis, periapical periodontitis, dentin hypersensitivity, gingival recession, etc., leading to the problem of delayed treatment.

For those who attach importance to oral health, they usually take a regular oral health examination every half year or year in medical institutions. However, in some cases, the pathogenic process of oral diseases is fast. When a patient goes to a medical institution for a regular oral health examination, oral diseases may have occurred, so that the problem of delayed treatment also exists.

In addition, before an oral treatment plan is carried out, it is currently difficult in the industry to demonstrate a comparison of changes in the appearance of the dentition before and after treatment.

When the patient goes to a medical institution for oral examination, a dentist can see the patient's dentition. At present, some medical institutions are able to show a three-dimensional true color model of the appearance of full dentition of the patient. However, it is currently difficult to show the patient the three-dimensional true color model of the appearance of full dentition of the patient after the patient has received oral treatment from the dentist. The specific numerical change in the appearance of the dentition before and after the treatment plan is completed is also currently difficult to quantitatively show the patient. The inventor have appreciated that two problems may be caused:

Problem I: The patient do not have an intuitive feeling about the effect of oral treatment, so that some oral treatments are less attractive to the patient. Therefore, some oral problems in the population, such as crowded dentition, dentition defects, gingival recession, dental plaque, pigmentation, etc., are not treated timely.

Problem II: It is difficult for the patient and dentist to create a quantitative convention for an oral treatment plan, which proposes a risk of medical disputes. For example: during orthodontic treatment, it sometimes needs to do stripping. Stripping, also known as "Interproximal Enamel Reduction", is the removal of a small amount of enamel from between the teeth to reduce their width so as to gain space necessary for orthodontics. Here, there are many requirements on the "removal of a small amount". The time, position and size of stripping all require professional design and precise operation. Generally, the size of stripping for a single tooth needs to be strictly controlled (within 0.2-0.5 mm), otherwise many negative problems may be caused, including tooth sensitivity caused by interproximal enamel reduction, vulnerability to dental caries after stripping, etc. However, the patient does not have an intuitive feeling about the position and size of stripping, and the dentist often does not inform the patient of the particular position and size of stripping in advance. Therefore, stripping is easy to become a blind spot in dentist-patient communication. A few medical institutions may make use of this blind spot in dentist-patient communication, and perform irreversible large-size stripping operation on the patient in the retainer stage in the late orthodontic treatment without authorization, which causes vulnerability of the patient to tooth sensitivity or even function impairment, thereby further inducing the patient to receive veneering or cosmetic crown treatment. Therefore, by inducing patients to receive excessive medical treatment, the purpose of making huge medical bills is achieved.

SUMMARY

In accordance with various embodiments disclosed herein, a tooth virtual editing method and system, a computer device, and a storage medium are provided.

In a first aspect of the present application, there is provided a tooth virtual editing method, the method comprising the following steps of:

Step S1, constructing a three-dimensional image basic database of a human oral cavity;

Step S2, acquiring three-dimensional image data of a user oral cavity, performing image pattern recognition on the three-dimensional image data according to the stored three-dimensional image basic database, recognizing an object to which the image data belongs, and establishing an object annotation system of the user oral cavity; and Step S3, performing virtual editing on the object according to the established object annotation system of the current user, and displaying an updated three-dimensional image of the teeth.

In a second aspect of the present application, there is provided a dental virtual editing system, comprising:
- a three-dimensional image basic database established according to big data of human oral cavities;
- an image data acquisition module for acquiring and obtaining three-dimensional image data of a user oral cavity and sending the three-dimensional image data to an image pattern recognition module;
- the pattern recognition module for receiving the three-dimensional image data sent by the image data acquisition module, retrieving from the basic database of the system, and recognizing an object to which the three-dimensional image data belongs;
- a virtual editing module for, according to the recognized object, performing virtual editing on the object; and
- a display module for displaying appearance of the edited three-dimensional image of user's teeth.

In a third aspect of the present application, there is provided a computer device comprising a memory and one or more processors, the memory having stored therein computer readable instructions which, when executed by the one or more processors, the one or more processors perform the steps of:

Step S1, constructing a three-dimensional image basic database of a human oral cavity;

Step S2, acquiring three-dimensional image data of a user oral cavity, performing image pattern recognition on the three-dimensional image data according to the stored three-dimensional image basic database, recognizing an object to which the image data belongs, and establishing an object annotation system of the user oral cavity; and Step S3, performing virtual editing on the object according to the established object annotation system of the current user, and displaying an updated three-dimensional image of the teeth.

In a fourth aspect of the present application, there is provided one or more non-transistory computer-readable storage media having stored therein computer-readable instructions that, when executed by one or more processors, the one or more processors perform the steps of:

Step S1, constructing a three-dimensional image basic database of a human oral cavity;

Step S2, acquiring three-dimensional image data of a user oral cavity, performing image pattern recognition on the three-dimensional image data according to the stored three-dimensional image basic database, recognizing an object to which the image data belongs, and establishing an object annotation system of the user oral cavity; and Step S3, performing virtual editing on the object according to the established object annotation system of the current user, and displaying an updated three-dimensional image of the teeth.

The details of one or more embodiments of the invention are set forth in the accompanying drawings and the description below. Other features and advantages of the present application will be apparent from the description, drawings, and claims.

BRIEF DESCRIPTION OF THE DRAWINGS

In order to more clearly illustrate the technical solutions in the embodiments of the present application, the drawings to be used in the embodiments will be briefly described below, and it is obvious that the drawings in the following description are merely some embodiments of the present application, and that other drawings can be obtained from these drawings without involving any inventive effort for those skilled in the art.

DETAILED DESCRIPTION

In order that the technical solutions and advantages of the present application may be more clearly understood, the present application is described in further detail below with reference to the accompanying drawings and examples. It should be understood that the specific embodiments described herein are merely illustrative of the present application and are not intended to be limiting thereof.

The application mainly aims to provide a visual tooth virtual editing method fix a user, so that the user is allowed to perform virtual editing operation on relevant parts of the teeth autonomously, and the appearance effect after the operation is performed is displayed. A dentist or a dental surgery robot may perform manual operation or programmed automatic operation on the teeth of a patient according to editing item list information preset in the system so as to realize the virtual editing content as actual operation.

Figure 1:
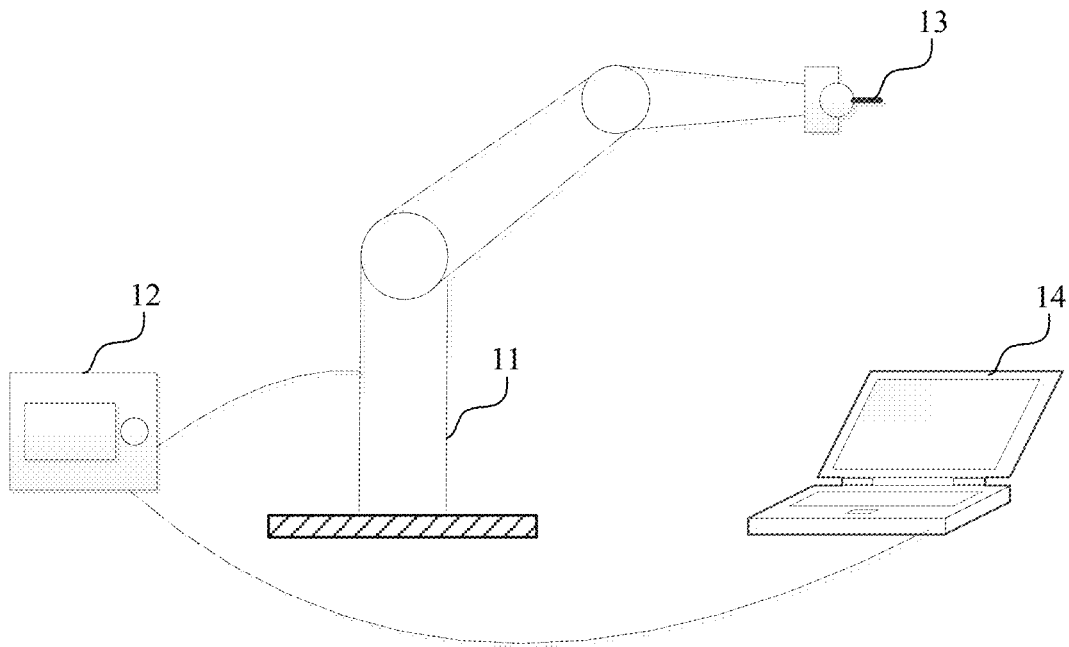
FIG. 1 is an application scenario diagram of a tooth virtual editing method in accordance with one or more embodiments.

The tooth virtual editing method provided herein may be applied in an application environment as shown in FIG. 1. A dental surgery robot 11 is connected to a robot controller 12 via a cable, and the robot controller 12 may provide control signals and power to the dental surgery robot 11. The dental surgery robot 11 may be equipped with an oral endoscope 13, which may include an endoscope body with a camera, a fill light, a temperature sensor and other devices. The robot controller 12 may be connected to a terminal 108 in a wired or wireless manner. The terminal 14 may be, but not limited to, various personal computers, notebook computers, smartphones, tablet computers, and portable wearable devices. It should be noted that the application environment of the tooth virtual editing method provided herein is not limited to the application environment shown in FIG. 1, but may also be applications, for example, in a system comprising an oral endoscope and a terminal, or in a system comprising an oral endoscope, a terminal and a server, in which the server may be implemented as a separate server or a server cluster composed of a plurality of servers, or may be a cloud server. In addition, the dental surgery robot 11, the robot controller 12 and the terminal 13 in FIG. 1 may be an integrated device, collectively referred to as a dental surgery robot.

Figure 2:
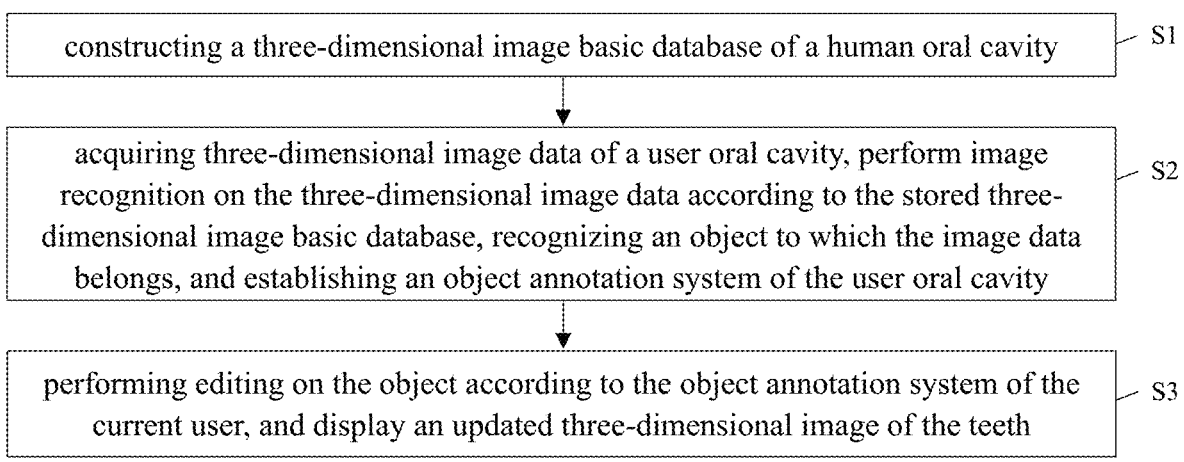
FIG. 2 is a flowchart of a tooth virtual editing method in accordance with one or more embodiments.

In one embodiment, referring to FIG. 2, there is provided a tooth virtual editing method, which is illustrated by taking application to the terminal in FIG. 1 as an example, comprising the following steps:

Step S1, constructing a three-dimensional image basic database of a human oral cavity.

Step S2, acquiring three-dimensional image data of a user oral cavity, performing image pattern recognition on the three-dimensional image data according to the stored three-dimensional image basic database, recognizing an object to which the image data belongs, and establishing an object annotation system of the user oral cavity; wherein the object comprises: a block anchor an entity; and wherein the block is formed by division according to curved surface images of different parts of the oral cavity, and the entity comprises: a tooth entity in a three-dimensional volume shape formed by enclosure of a plurality of blocks associated with a tooth part, and a dentition entity formed by combination of a plurality of tooth entities and gaps between the tooth entities.

Step S3, virtual editing is performed on the object according to the established oral cavity annotation system of the current user, and an updated three-dimensional image of user's teeth is displayed.

In the embodiments of the present application, performing editing on an object includes performing editing on a block, or only performing editing on an entity, and further includes performing editing on both a block and an entity. When performing editing on a block, the image data directly acquired is the curved surface image of the user oral cavity, and when an entity is edited, the image data directly acquired is a three-dimensional entity image of teeth or dentition of the user oral cavity.

In one embodiment, the Step S2 further comprises:

Step S21, firstly, performing image pattern recognition on the three-dimensional image data, a block to which the image data belongs is recognized, outputting a recognition result, and establishing a block annotation system of the user oral cavity; and Step S22, then, establishing an entity annotation system covering the user's teeth according to image information of each block in the block annotation system and a spatial relationship between the blocks.

That is, firstly, performing block division according to the curved surface image to form a block and an annotation system thereof, and then giving the divided blocks, image information of each block and a spatial relationship between the blocks to form an entity and an entity annotation system thereof. The entity includes an individual tooth and a dentition formed by arrangement of teeth.

The above steps of the embodiments of the present application will be described in detail below.

In the Step S1, the three-dimensional image basic database of the human oral cavity is constructed based on various conditions of the human oral cavity, and the three-dimensional image basic database stores general framework data of a three-dimensional image model of the human oral cavity in various scenarios. The scenarios include a normal healthy oral cavity scenario, a dirty oral cavity scenario, a pathological oral cavity scenario, a deformed oral cavity scenario, an injured oral cavity scenario, and a mixed dentition stage scenario in which deciduous teeth grow to replace permanent teeth, of adults, and further include a normal healthy oral cavity scenario, a dirty oral cavity scenario, a pathological oral cavity scenario, a deformed oral cavity scenario, an injured oral cavity scenario and a deciduous tooth eruption stage scenario of children.

The adults and children herein may also include adults and children in different age stages, for example, adults may be classified as 18-28 years old, over 28 years old, and so on, and minors may be classified as before 2 years old, over 2 years old, and so on, although not limited to the above classification.

In the Step S2, three-dimensional true color scanning is performed on a user oral cavity surface (at least containing all dentition parts) to acquire spatial arrangement and digital three-dimensional true color curved surface image data cover the whole user oral cavity surface, and the scanning may be performed by using an oral endoscope on specific part, or may be performed partially, that is, only the three-dimensional curved surface image of a part to be subjected to editing is acquired. In this embodiment, the spatial arrangement of full-mouth teeth of the user includes not only a spatial position relationship between the teeth, but also an occlusal relationship of a maxillary dentition and a mandibular dentition. In the block annotation system containing the occlusal relationship of dentition, the annotation information of some blocks of the maxillary dentition contains a spatial position relationship information between the block itself and adjacent blocks of the maxillary dentition, and also contains a spatial position relationship information between the block itself and adjacent blocks of the mandibular dentition; and the annotation information of some blocks of the mandibular dentition contains a spatial position relationship information between the block itself and adjacent blocks of the mandibular dentition, and also contains a spatial position relationship information between the block itself and adjacent blocks of the maxillary dentition. The process of obtaining an occlusal relationship includes two cases, i.e. in an occlusal state or an open state. When the maxillary dentition and the mandibular dentition of the user are in the occlusal state, namely when the maxillary dentition and the mandibular dentition abut against each other, scanning is performed on the user oral cavity to comprehensively scan the labial and buccal sides of the dentition of the user at least from the side of the vestibule of the oral cavity, thereby obtaining images of occluded maxillary dentition and mandibular dentition, and judging the spatial position between the maxillary dentition and the mandibular dentition with the occluded images so as to judge whether the maxillary dentition and the mandibular dentition are aligned; and when the maxillary dentition and the mandibular dentition of the user are in the open state, namely when the maxillary dentition and the mandibular dentition are separated, scanning is also performed on the user oral cavity to obtain a three-dimensional true color image of the cutting surface and the occlusal surface as well as the lingual side and the palatal side of the user's teeth, thereby judging whether the dentitions are neat or not. The scanning herein includes scanning the inside and outside of the oral cavity.

After the digital three-dimensional true color image of the oral cavity surface is obtained, image pattern recognition is performed on the digital three-dimensional true color model of the user dentitions according to the image pattern recognition module and the three-dimensional image basic database stored in the system, so that the block to which each part of the teeth in the model belongs may be recognized, and the recognition result is output in a form of block annotation information of the image. The recognition may be effectively performed in particular by true color scanning. According to the recognition result, the system assigns a block name and a corresponding block serial number to each block of the full-mouth teeth of the user according to a predetermined rule, and acquires corresponding spatial arrangement data (a spatial position of the block and a connection boundary between the block and other blocks) and block shape data (three-dimensional curved surface shape data of the block), thereby forming the block annotation system of the full-mouth teeth of the user. The blocks herein are formed by division according to the curved surface images of different parts of the oral cavity. The principle and process of the division of the blocks will be described in detail in the following.

In one embodiment, scanning is also performed on face and oral fissure regions near the lips when the user lips are closed or opened to obtain an oral cavity surface image visible from the outside in the user oral fissure region, image pattern recognition is performed on the oral cavity image visible in the user oral fissure region according to the stored three-dimensional image basic database, a block to which the oral cavity surface visible in the oral fissure region belongs is recognized, a recognition result is output, and a block annotation system of the user face and oral fissure regions is established.

In this embodiment, the scanning on the lips and oral fissure regions on the face includes two cases, namely, the lips are in a closed calm state or in an mouth-opened teeth exposing state, wherein the mouth-opened teeth exposing state may be further divided into a smile state and a mouth-opened laugh state; in the closed state, the dentitions are not visible, and in the smile state, only a small part of teeth are exposed (e.g., mainly the labial surface of the incisors of the maxillary dentition), and in the mouth-opened laugh state, most tooth surfaces are exposed.

If the scanning recognition is performed individually on the teeth in the oral cavity, it can only recognize whether an individual tooth has a problem or not, such as caries cavities in the occlusal surface of the tooth, gingival crevicular redness, dental plaque, tooth absence and other common tooth problems, but cannot recognize problems in the spatial relationship of the teeth, such as buckteeth, malocclusions and the like, and these problems should be judged according to the relative position relationship between the maxillary and mandibular dentitions in the occlusal state or the scanning of the face region outside the oral cavity. Therefore, scanning on user maxillary and mandibular dentitions in the occlusal state, and the lips and oral fissure regions on the face are provided herein, so that it can be judged whether the user has a problem belonging to the problems relating to the spatial relationship of the teeth or not, such as buckteeth, malocclusions and the like, and it can more accurately recognize the tooth problems of the user in various scenarios.

In the step S22, a tooth entity annotation system covering all user's teeth is established according to the digital three-dimensional true color image of the user oral cavity surface and the block system formed by a plurality of established blocks which are mutually connected. The tooth entity is formed by enclosure of a plurality of blocks associated with a tooth part, and is in a three-dimensional volume shape. The system assigns corresponding tooth entity annotation information to each tooth entity, and the tooth entity annotation information is established based on a plurality of mutually connected blocks associated with each tooth and their block annotation information. The tooth entity annotation information comprises a tooth entity name assigned according to a predetermined rule, a corresponding tooth entity serial number, corresponding spatial arrangement data (a spatial position of the tooth entity and a connection boundary between the tooth entity and other tooth entities), and tooth entity shape data (three-dimensional curved surface shape data enclosing the tooth entity), thereby forming the tooth entity annotation system covering the full-mouth teeth of the user.

In the step S22, a dentition entity annotation system of the maxillary and mandibular dentitions of the user is established according to the acquired digital three-dimensional true color image of the user, the block system, and the tooth entity annotation system covering user full-mouth teeth.

A three-dimensional dentition entity of the maxillary dentition of the user is formed by enclosure of tooth entities in the maxillary dentition of the user, gaps between the tooth entities and gingival blocks of the maxillary alveolar ridge of the user. A three-dimensional dentition entity of the mandibular dentition of the user is formed by enclosure of tooth entities in the mandibular dentition of the user, gaps between the tooth entities and gingival blocks of the mandibular alveolar ridge of the user.

The system assigns corresponding dentition annotation information to the maxillary dentition entity and the mandibular dentition entity. The dentition entity annotation information comprises a dentition entity name (e.g., the maxillary dentition or the mandibular dentition) assigned according to a predetermined rule, a corresponding dentition entity serial number (e.g., 1 refers to the maxillary dentition and 2 refers to the mandibular dentition), corresponding spatial arrangement data (i.e., a relative position relationship between the maxillary dentition and the mandibular dentition of the user when they are occluded), dentition entity image data (namely, three-dimensional curved surface image data enclosing the dentition), thereby forming the dentition entity annotation system covering the maxillary dentition and the mandibular dentition of the user.

In the step S3, editing is performed on the operation object according to the currently established block annotation system and entity annotation system, and an updated three-dimensional image of the teeth is displayed.

As the three-dimensional curved surface of the user oral cavity is divided into a plurality of blocks and entities, on one hand, the user may perform virtual editing on the teeth of the user according to personal preferences, on the other hand, an offending object, which is obtained through image pattern recognition according to the three-dimensional image basic database by the system, namely a block or a tooth entity or dentition entity with a pathological problem, is annotated and edited, and the updated three-dimensional image of the teeth is displayed. Among others, the editing is performed according to editing item list information stored in the basic database stored in the system, and the editing item list information comprises: a serial number of the operation object, an editing content and an appearance image after editing, so that it can be determined which part in which region is subjected to editing according to the serial number of the operation object, and the editing content is an editing action for the operation object and editing parameters. In this embodiment, the editing action includes: removing dental plaque on a block, removing dental calculus on a block, removing pigment on a block, repairing a curved surface shape of a block, rotating a tooth entity, moving a tooth entity, stripping a tooth entity, performing veneering or cosmetic crown treatment on a tooth entity, and repairing an inlay of a tooth entity; and the parameter settings include: specific quantized numerical parameters and value ranges of the editing action, such as a translation distance, a rotation angle, a stripping depth, a removal area and so on.

Based on the constructed three-dimensional image basic database of the human oral cavity, image pattern recognition is performed on the three-dimensional image data of the user oral cavity obtained by scanning, so that three-dimensional curved surface image data or three-dimensional entity image data with a pathological problem is classified into a specific block or entity and is annotated, thereby completing the process of discovering a tooth pathological problem.

Specifically, in this embodiment, the three-dimensional image basic database of the human oral cavity stores three types of data, the first type of data is three-dimensional curved surface image data of all regions of the human oral cavity surface, the second type of data is three-dimensional entity image data of the human oral cavity, and the third type of data is editing item list information for performing editing on the operation object (block and entity).

The first type of data, i.e. the three-dimensional curved surface image data of all regions of the human oral cavity surface, is oriented to establishing of the block annotation system. The three-dimensional curved surface image data comprises a pre-divided three-dimensional image and annotation information of blocks to which the image belongs, wherein the three-dimensional curved surface image is pre-divided into a plurality of mutually connected blocks, and annotation information is established for each block, the annotation information containing image information of the block, a spatial position relationship between adjacent blocks, and a spatial position relationship between a certain maxillary dentition block and a corresponding mandibular dentition block abutting the maxillary dentition block, as well as a spatial position relationship between a certain mandibular dentition block and a corresponding maxillary dentition block abutting the mandibular dentition block in the occlusal state.

In one embodiment, during block division, the three-dimensional image of the oral cavity surface may be divided directly into blocks, or of course, may be firstly divided into regions, and then each region is divided into blocks, that is, the oral cavity surface is firstly divided into a series of mutually connected regions and then the curved surface images of the regions are divided into one or more connected blocks. Such division is more efficient and is not limited in the embodiments of the present application.

In the following, a detailed description will be given taking the case of performing region division first.

A. Region

In one embodiment, the division of regions may be based on the function of each part of the oral cavity. Also, each region has at least one serial number information.

For example, the full-mouth teeth surface of the user may be divided into six regions: a left occlusal clearance region, a right occlusal clearance region, a maxillary dentition region, a mandibular dentition region, a maxillary alveolar ridge bottom surface region and a mandibular alveolar ridge top surface region. Among others, each region corresponds to one serial number information, for example, 1, 2, 3, 4, 5 and 6 in sequence.

In particular, the division of the regions of the oral cavity surface is not limited in the embodiments of the present application, while the purpose is to divide the oral surface into distinguishable regions which may be joined to form a complete oral surface.

B. Block

In one embodiment, during the division of blocks, the following principles are followed: a block should has an interior with a single texture a single color as far as possible, and is approximately planar as far as possible. The size and the specific shape of the block are not limited in the embodiments of the present application, and may be determined through comprehensive consideration about the precision requirement and the calculation amount requirement of the three-dimensional image.

In one embodiment, the surface connection relationship and relative spatial position relationship between each block and other blocks are systematically sorted and described. Each block has its own unique tag (e.g., the name and its serial number) and related image feature information, etc., so that a complete block annotation system is established, each block can be found quickly, and the image feature information of each block can be obtained.

Among others, each block is established with respective annotation information, and the annotation information contains image information of the block, a spatial position relationship between adjacent blocks, and a spatial position relationship between a maxillary dentition block and a corresponding mandibular dentition block abutting the maxillary dentition block, as well as a spatial position relationship between a mandibular dentition block and a corresponding maxillary dentition block abutting the mandibular dentition block in the occlusal state, and may further contains name information of the block, file attribute description information, etc. Among others, the image information of the block contains: an image serial number and image feature information of the block, and may further contain sample instance information of the three-dimensional curved surface image of the block, and the image feature information contains information such as shape, color, texture and boundary features of each block.

For example, for a maxillary dentition region with a serial number of 3, it may be divided into multiple blocks, for example: Block (3.1.1), mesial surface block of tooth upper left 1. Block (3.1.2), labial side surface block of tooth upper left 1.

Similarly, in the embodiments of the application, the division of the blocks in the region is not limited, and the division may be performed according to actual conditions while ensuring that each block can be combined to form a complete corresponding region.

That is to say, in the embodiments of the present application, in the constructed three-dimensional image frame database, not only the oral cavity is divided into the regions and blocks, but also the block annotation system is established, so that the positions in the oral cavity can be accurately identified, providing convenience for three-dimensional image matching and reconstruction. In addition, an image processing device in the present application is allowed to obtain semantic information of image data received from an endoscope in the process of processing the received image data, and conditions are created for performing oral endoscopic image examination using artificial intelligence technology.

Figure 3:
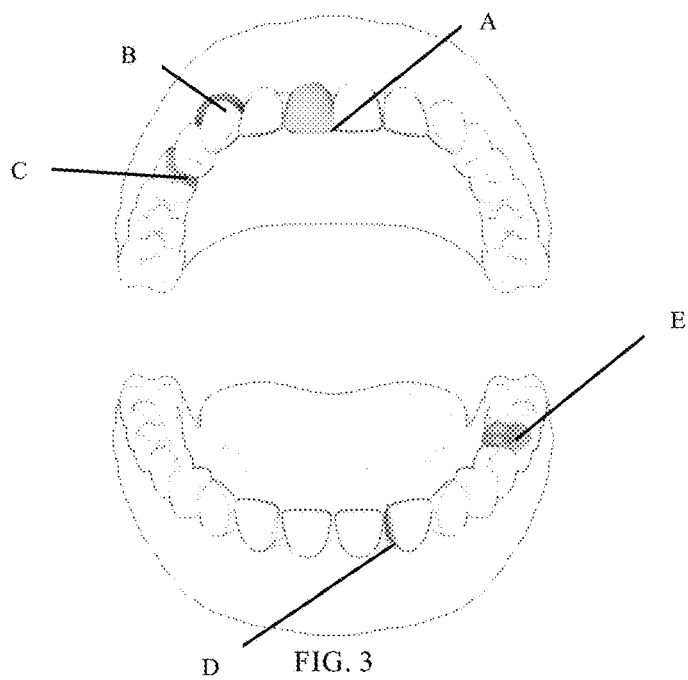
FIG. 3 is a schematic diagram illustrating selection and annotation of part of blocks in accordance with one or more embodiments.

With regard to the annotation of the blocks, reference is made to FIG. 3, FIG. 2 shows a plurality of blocks annotated on an image obtained by scanning. Including: an upper left 1 labial side surface block A, an upper left 3 tooth labial side gingival crevicular block B, an upper left 5 mesial integroximal surface block C, a lower right 2 mesial interproximal surface block D and a lower right 6 occlusal surface block E.

The second type of data, i.e. the three-dimensional entity image data of the human oral cavity, is oriented to establishing of the block annotation system. The three-dimensional entity image data contains annotation information of a corresponding entity, the annotation information containing three-dimensional image data of the entity, a spatial position relationship between adjacent entities, and a spatial position relationship between a certain maxillary dentition entity and a corresponding mandibular dentition entity abutting the maxillary dentition entity, as well as a spatial position relationship between a certain mandibular dentition entity and a corresponding maxillary dentition entity abutting the mandibular dentition entity in the occlusal state. The entity comprises: a tooth entity in a three-dimensional volume shape formed by enclosure of a plurality of blocks associated with a tooth part, and a dentition entity formed by combination of a plurality of tooth entities and gaps between the tooth entities (including a maxillary dentition entity and a mandibular dentition entity).

For example, a three-dimensional tooth entity of each upper anterior tooth is formed by enclosure of three-dimensional curved surface images to which a labial side surface block, a labial gingival crevicular block, a palatal side surface block, a palatal side gingival crevicular block, a mesial interproximal surface block, a mesial interproximal surface gingival crevicular block, a distal interproximal surface block, a distal interproximal surface gingival crevicular block, and a cutting surface block related to the tooth belong. A three-dimensional tooth entity of each lower molar is formed by enclosure of three-dimensional curved surface images to which a buccal side surface block, a buccal side gingival crevicular block, a lingual side surface block, a lingual side gingival crevicular block, a mesial interproximal surface block, a mesial interproximal surface gingival crevicular block, a distal interproximal surface block, a distal interproximal surface gingival crevicular block, and an occlusal surface block related to the tooth belong.

With the popularization and use of the method and the system provided herein, the three-dimensional image basic database of the human oral cavity of the application may also be continuously updated and expanded, for example, objects in new pathological oral cavity scenarios and their annotation information may be added, or objects in new injured oral cavity and their annotation information may be added, the annotation information containing data such as three-dimensional image data of the block, a spatial position relationship between adjacent blocks and the like. In this way, the accuracy of matching may be further improved. Specifically, when the recognition for the image data obtained by scanning cannot be achieved by system based on the current basic database, the image data is uploaded to a cloud server by the system for artificial recognition to input the annotation information, then the basic database is updated according to the recognition result and the annotation information, and iterative training may be performed on the image pattern recognition module according to a big-data AI training algorithm, thereby improving the accuracy of data matching.

The third type of data is editing item list information for performing editing on an operation object (block and entity). The editing item list information comprises: a serial number of the operation object, an editing content and an appearance image after editing, the editing content comprising an editing action for the operation object and parameter settings for the editing action. The editing action includes: removing dental plaque on a block, removing dental calculus on a block, removing pigment on a block, repairing a curved surface shape of a block, rotating a tooth entity, moving a tooth entity, stripping a tooth entity, performing veneering or cosmetic crown treatment on a tooth entity, and repairing an inlay of a tooth entity; and the parameter settings include: specific quantized numerical parameters and value ranges of the editing action, such as a translation distance, a rotation angle, a stripping depth, a removal area and so on. The system gives every object (block and entity) a feasible and quantitative item list information, the user performs editing operation in a given parameter range, and the new appearance effect after the editing operation is displayed. Through the object-oriented virtual editing operation, the user (a consumer or a doctor) can determine by him/herself the operation part and the quantized value of the operation, and the appearance effect after the operation is performed is displayed to the user, thereby achieving a human-computer interaction function. The object for virtual editing includes all the blocks and entities, and the entities include tooth entities and dentition entities. By performing virtual editing operation on the objects in the oral cavity, a user can carry out virtual treatment operations such as virtual repairing, virtual orthodontic and virtual beautification on the oral cavity. Besides, the virtual editing operation can output a specific operation position, a specific operation direction and a corresponding quantitative value, as well as the appearance of the object (a dentition three-dimensional true color model containing the appearance of the object) after the operation is performed.

Figure 4:
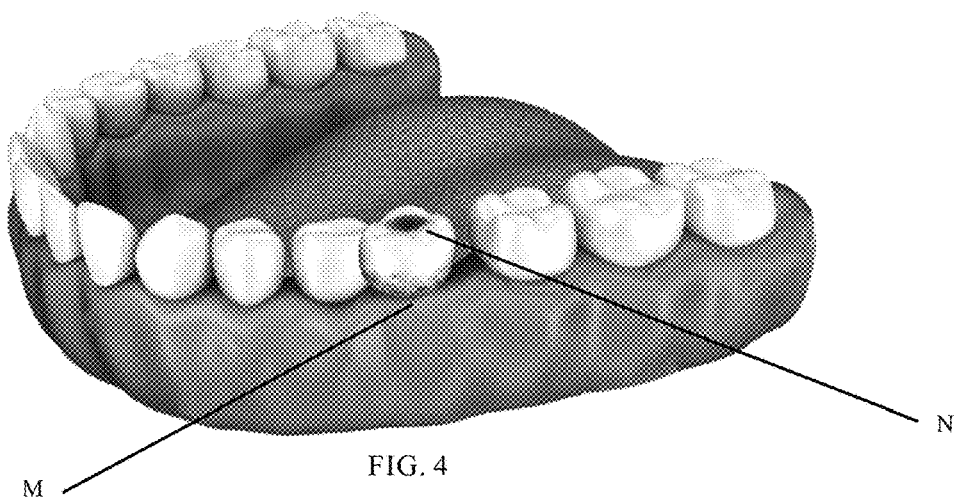
FIG. 4 is a photographic representation of a pathological problem existing in user dentition obtained by scanning in accordance with one or more embodiments.
Figure 5:
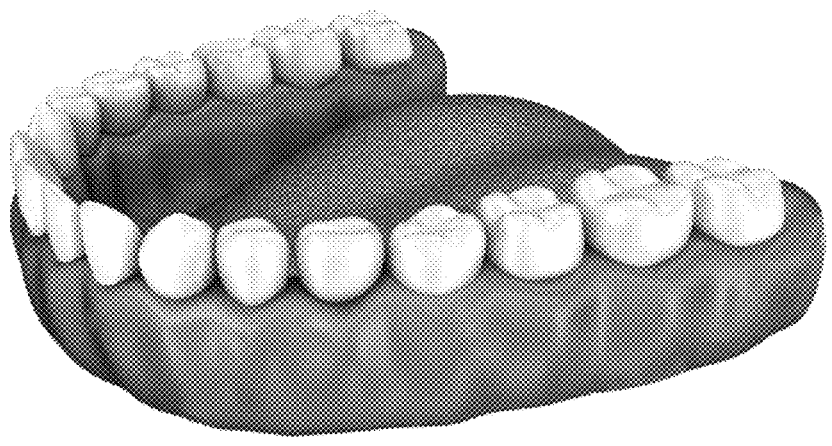
FIG. 5 is a photograph representation after virtual editing in accordance with one or more embodiments.

For example, through three-dimensional true color scanning, the system detects that in a teeth image of a user, a tooth lower right 5 has a plaque M in the gingival crevicular and a caries cavity N in the occlusal surface, and the tooth lower right 5 is too close to the tooth lower right 4, as shown in FIG. 4. In this way, after the matching by the system, editing may be performed for the above three problems according to the displayed item list information, which specifically includes operations such as moving the tooth towards right, repairing the caries cavity, and removing the plaque, and may further include operations such as whitening the teeth, and the appearance after repairing is obtained, as shown in FIG. 5. The dentist or the dental surgery robot can perform actual surgery operation on the user's teeth according to the editing content preset by the system.

Among others, in a case of adding a new object and annotation information thereof into the basic database after artificial recognition, the editing item list information of the object is added into the basic database by manual operation, and in a case of revising the annotation information of an existing object in the basic database without adding a new object after artificial recognition, whether to adaptively revise original editing item list information of the existing object in the basic database is determined by manual operation. In particular, in the case of adding a new recognition object (block or entity), the editing item list information of the object needs to be correspondingly added into the basic database, and in the case of only adding annotation information (such as image sample data and image feature information) of an existing object, analysis may be performed artificially to determine whether the content of the original editing item list information of the existing object in the basic database needs to be adaptively revised or not, and if the content needs to be revised, the item list information is adaptively revised, and after the editing item list information in the basic database is updated, the editing content is enriched, and the editing function becomes more powerful.

It should be understood that although the steps in the flowchart of FIG. 2 are shown sequentially as indicated by the arrows, these steps are not necessarily performed sequentially as indicated by the arrows. Unless specifically stated otherwise herein, the steps are not performed in a strict order of limitation, and the steps may be performed in other orders. Moreover, at least a part of the steps in FIG. 2 may include a plurality of sub-steps or stages that are not necessarily performed at the same time, but may be performed at different times, and the order in which the sub-steps or stages are performed is not necessarily sequential, but may be performed in alternation or alternation with at least a part of the sub-steps or stages of other steps or steps.

Figure 6:
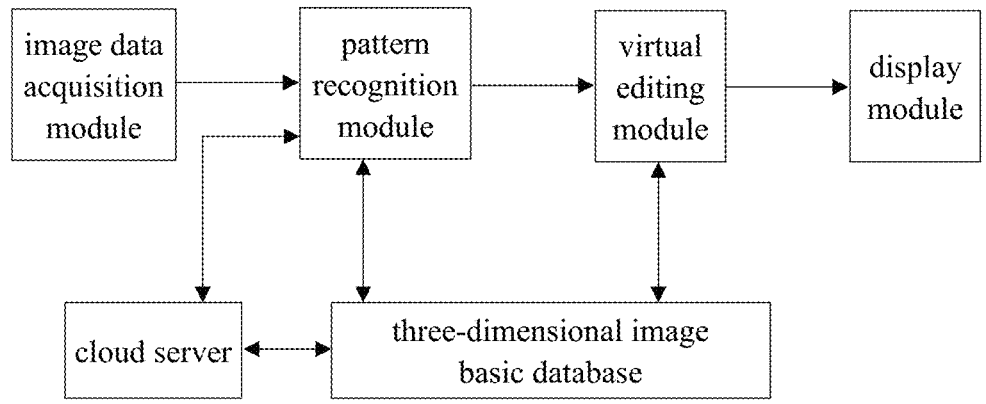
FIG. 6 is a schematic diagram showing the structure of a tooth virtual editing system in accordance with one or more embodiments.

Referring to FIG. 6, another embodiment of the present application discloses a dental virtual editing system, wherein the system comprises: a three-dimensional image basic database, an image data acquisition module, a pattern recognition module, a virtual editing module and a display module.

The three-dimensional image basic database is established according to big data of human oral cavities; and the three-dimensional image basic database of the human oral cavity stores three-dimensional image data of the human teeth in various scenarios, and item list information for performing editing on a related object.

The image data acquisition module is used for acquiring and obtaining three-dimensional image data of a user oral cavity and sending the three-dimensional image data to an image pattern recognition module.

The pattern recognition module is used for receiving the three-dimensional image data sent by the image data acquisition module, retrieving from the basic database of the system, and recognizing an object to which the three-dimensional image data belongs; the object comprises a block and/for an entity; wherein the block is formed by division according to curved surface images of different parts of the oral cavity, and the entity comprises: a tooth entity in a three-dimensional volume shape formed by enclosure of a plurality of blocks associated with a tooth part, and a dentition entity formed by combination of a plurality of tooth entities and gaps between the tooth entities.

The virtual editing module is used for, according to the recognized object, performing virtual editing on the object; and the editing may be performed on a block or an entity. The blocks herein are formed by division according to the curved surface images of different parts of the oral cavity, and the entity comprises: a tooth entity in a three-dimensional volume shape formed by enclosure of a plurality of blocks associated with a tooth part, and a dentition entity formed by combination of a plurality of tooth entities and gaps between the tooth entities.

The display module is used for displaying appearance of the edited three-dimensional image of user's teeth, such that the user is enabled to have an intuitive feeling about the change in the teeth.

The pattern recognition module may perform pattern recognition on the three-dimensional image data of the user oral cavity according to annotation information of a block and entity stored in the basic database and determines a serial number of the block or entity to which the image data belongs. The virtual editing module indexes the serial number of the block or entity to a certain block or entity so as to obtain the image information of the block or entity quickly and retrieve editing item list information of the block or entity in the basic database, thereby achieving editing operation on the teeth.

The system further comprises a cloud server connected with both the pattern recognition module and the three-dimensional image basic database, wherein when the recognition for the image data send by the image acquisition module cannot be achieved by the pattern recognition module, the image data is sent to the cloud server for artificial recognition to input the annotation information and revise the editing item list information, and then the basic database is updated according to the artificial recognition result, the annotation information and the editing item list information. In particular, in the case of adding a new object (block or entity), the editing item list information of the object needs to be correspondingly added, and in the case of only adding an image sample of an existing object, analysis may be performed artificially to determine whether the content of original editing item list information of the existing object needs to be adaptively revised or not, and it may be revised or not revised, depending on the actual situation. After the three-dimensional image basic database is updated, the cloud server performs iterative training on the pattern recognition module based on the updated basic database. Then, the cloud server updates each pattern recognition module deployed in the system into a trained version of the pattern recognition module, so that the accuracy of data matching is improved. After the editing item list information in the basic database is updated, the editing content retrieved by the virtual editing module from the database is enriched, and the editing function becomes more powerful.

The above system is used for executing the method in the embodiments of the present application, and reference may be made to the method in the previous embodiments where the system in this embodiment is not exhaustive.

According to the present application, based on the image data of the user oral cavity and the shape and arrangement of the full-mouth teeth of the user, a daily artificial intelligence examination function for oral health is provided, and potential health risks can be found in time. A virtual editing function for performing virtual treatment operation on a tooth model is provided, and has the effects of determining quantitative values and displaying the appearance effect. A human-computer interaction function for performing virtual treatment operation on a dentition model is also provided, and has the effects of determining quantitative values and displaying the appearance effect. Thereafter, manual operation or programmed automatic operation is performed on the teeth of a patient so as to realize the virtual editing content as actual operation.

According to one or more embodiments of the present application, by acquiring routine intra-oral optical image data, automatic intelligent diagnosis for various pathological symptoms is performed according to the three-dimensional image basic database of the human oral cavity and the pattern recognition algorithm, so that potential health risks of the oral cavity dentitions can be found in time, thereby preventing delay in treatment.

According to one or more embodiments of the present application, the user is provided with the function of performing virtual treatment operation on the dentition model, such as: virtual repairing, virtual orthodontic and virtual beautification, and an operation part and a corresponding quantitative value of the treatment operation is provided to the user, and the appearance effect after the operation is performed is displayed to the user. Therefore, the doctor-patient communication between the dental patient and the dentist becomes more open, transparent, accurate, smooth and convenient.

According to one or more embodiments of the present application, the intefacting between dental clinician and the dental surgery robot is facilitated. According to the invention, the dental surgery robot can perform preprogrammed automatic operation on the teeth of the patient according to the editing content preset in the system (an editing action for the operation object and parameter settings of the editing action) so as to realize the virtual editing content as actual operation.

Figure 7:
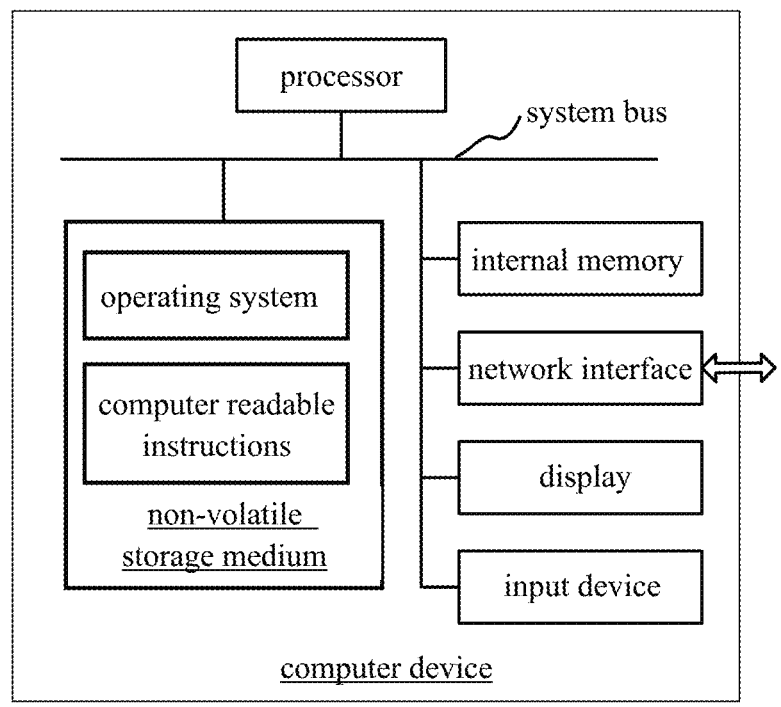
FIG. 7 is a block diagram of a computer device in accordance with one or more embodiments.

In one embodiment, a computer device is provided, which may be a terminal, the internal structure of which may be as shown in FIG. 7. The computer device comprises a processor, a memory, a network interface, a display, and an input device which are connected via a system bus. Among others, the processor of the computer device is used for providing computing and control capability. The memory of the computer device comprises a non-volatile storage medium and an internal memory. The non-volatile storage medium stores an operating system and computer readable instructions. The internal memory provides an environment for running the operating system and computer-readable instructions in the non-volatile storage medium. The network interface of the computer device is used for communicating with an external terminal through a network connection. The computer readable instructions are executed by the processor to implement the tooth virtual editing method. The display of the computer device may be a liquid crystal display or an electronic ink display, the input device of the computer device may be a touch layer coating the display, or may be a key, a track ball or a touch pad arranged on the casing of the computer device, or may be an external keyboard, touch pad or mouse.

It will be understood by those skilled in the art that the structure shown in FIG. 7 is merely a block diagram of a part of the structure associated with the solution of the application and does not constitute a limitation on the computer device to which the solution of the application may be applied, and that a particular computer device may include more or fewer components than those shown in the drawings, or may combine certain components, or may have a different arrangement of components.

A computer device comprising a memory and one or more processors, the memory having stored therein computer readable instructions which, when executed by the processors, carry out the steps of the method provided in any one of the embodiments of the present application.

One or more non-transistory storage media having stored therein computer-readable instructions that, when executed by one or more processors, the one or more processors perform the steps of the method provided in any one embodiment of the present application.

While the foregoing description has shown and described several preferred embodiments of the present application, it is to be understood that the application is not limited to the forms disclosed herein, but is not to be construed as excluding other embodiments. Various other combinations, modifications, and environments may be used, and modifications may be made within the scope of the inventive concepts described herein, by techniques or knowledge of the above guidance or related art. Modifications and variations by those skilled in the art are intended to be within the scope of the claims appended hereto without departing from the spirit and scope of the present application.

What is claimed is:

1. A tooth virtual editing method, comprising the steps of:
    Step S1, constructing a three-dimensional image basic database of a human oral cavity;
    Step S2, acquiring three-dimensional image data of a user's oral cavity, performing image pattern recognition on the three-dimensional image data according to the stored three- dimensional image basic database, recognizing an object to which the three-dimensional image data belongs, and establishing an object annotation system of the user's oral cavity; and
    Step S3, performing virtual editing on the object according to the established object annotation system of the user's oral cavity, and displaying an updated three-dimensional image of user's teeth,
    wherein said acquiring three-dimensional image data of the user's oral cavity comprises performing three-dimensional true color scanning on the user's oral cavity to obtain a spatial arrangement of the user's teeth and a three-dimensional true color curved surface image of the user's teeth, wherein the spatial arrangement comprises relationships between the teeth and an occlusal relationship between a maxillary dentition and mandibular a dentition in an occlusal state.

2. The tooth virtual editing method according to claim 1, wherein the object comprises: a block and/or an entity, wherein the block is formed by division according to curved surface images of different parts of the oral cavity, and the entity comprises: a tooth entity in a three-dimensional volume shape formed by enclosure of a plurality of blocks associated with a tooth part, and a dentition entity formed by combination of a plurality of tooth entities and gaps between the tooth entities.

3. The tooth virtual editing method according to claim 2, wherein the Step S2 further comprises:
    Step S21, performing image pattern recognition on the three-dimensional image data, recognizing a block to which the image data belongs, outputting a recognition result, and establishing a block annotation system of the user's oral cavity; and
    Step S22, establishing an entity annotation system covering the user's teeth according to image information of each block in the block annotation system and a spatial relationship between the blocks.

4. The tooth virtual editing method according to claim 3, wherein the three-dimensional image basic database of the human oral cavity stores three-dimensional curved surface image data and three-dimensional entity image data covering all regions of a human oral cavity surface, and editing item list information for performing editing on the object.

5. The tooth virtual editing method according to claim 4, wherein said editing item list information comprises: a serial number of an editing object, an editing content and an appearance image after editing, wherein the editing content contains an editing action for the operation object and parameter settings for the editing action.

6. The tooth virtual editing method according to claim 5, wherein the editing action comprises: removing dental plaque on a block, removing dental calculus on a block, removing pigment on a block, repairing a curved surface shape of a block, rotating a tooth entity, moving a tooth entity, stripping a tooth entity, performing veneering or cosmetic crown treatment on a tooth entity, and repairing an inlay of a tooth entity; and the parameter settings include: specific quantized numerical parameters and value ranges of the editing action.

7. The tooth virtual editing method according to claim 1, wherein the method further comprises: performing scanning on user's face and user's oral fissure regions near user's lips when the user's lips are closed or opened to obtain an oral cavity surface image visible from the outside in the user's oral fissure region, performing image pattern recognition on the oral cavity image visible in the user's oral fissure region according to the stored three-dimensional image basic database, recognizing a block to which the oral cavity surface visible in the user's oral fissure region belongs, outputting a recognition result, and establishing a block annotation system of the user's face and the user's oral fissure regions.

8. The tooth virtual editing method according to claim 7, wherein the three-dimensional image basic database pre-stores three-dimensional curved surface image data of human teeth in various scenarios, the three-dimensional curved surface image is pre-divided into a plurality of mutually connected blocks, and annotation information is established for each said block, the annotation information containing image information of the block, a spatial position relationship between adjacent blocks, and a spatial position relationship between a certain maxillary dentition block and a corresponding mandibular dentition block abutting the maxillary dentition block, as well as a spatial position relationship between a certain mandibular dentition block and a corresponding maxillary dentition block abutting the mandibular dentition block in the occlusal state; and
    the three-dimensional image basic database further pre-stores three-dimensional entity image data of human teeth in various scenarios, and the three-dimensional entity image data contains annotation information of a corresponding entity, the annotation information containing three-dimensional image data of the entity, a spatial position relationship between adjacent entities, and a spatial position relationship between a certain maxillary dentition entity and a corresponding mandibular dentition entity abutting the maxillary dentition entity, as well as a spatial position relationship between a certain mandibular dentition entity and a corresponding maxillary dentition entity abutting the mandibular dentition entity in the occlusal state.

9. The tooth virtual editing method according to claim 8, wherein pre-dividing the three-dimensional curved surface image into a plurality of mutually connected blocks comprises: firstly dividing the oral cavity surface into a series of mutually connected regions, and then dividing a curved surface image of a region into one or more mutually connected blocks.

10. The tooth virtual editing method according to claim 4, wherein according to the three-dimensional image basic database, the acquired image data is matched with image data of a corresponding object stored in the three-dimensional image basic database according to a preset image pattern recognition algorithm to obtain a mapping relationship therebetween, an offending object is determined in the three-dimensional image of the user's teeth according to the mapping relationship, and editting is performed on the offending object.

11. The tooth virtual editing method according to claim 4, wherein when the recognition for the acquired image data cannot be achieved based on the current basic database, the image data is uploaded to a cloud server for artificial recognition to input the annotation information or revise the editing item list information, and then the basic database is updated according to the recognition result, the annotation information and the editing item list information.

12. The tooth virtual editing method according to claim 11, wherein in a case of adding a new object and annotation information thereof into the basic database after artificial recognition, the editing list information of the object is added into the basic database by manual operation, and in a case of revising the annotation information of an existing object in the basic database without adding a new object after artificial recognition, whether to adaptively revise original editing item list information of the existing object in the basic database is determined by manual operation.

13. A tooth virtual editing device, comprising:
 a three-dimensional image basic database established according to big data of human oral cavities;
 an image data acquisition device for acquiring and obtaining three-dimensional image data of a user's oral cavity and sending the three-dimensional image data to an image pattern recognition device;
 the image pattern recognition device for receiving the three-dimensional image data sent by the image data acquisition device, retrieving from the three-dimensional image basic database, and recognizing an object to which the three-dimensional image data belongs;
 a virtual editing device for, according to the recognized object, performing virtual editing on the three-dimensional image of the object; and
 a display device for displaying appearance of the edited three-dimensional image data of
 wherein said acquiring three-dimensional image data of the user's oral cavity comprises performing three-dimensional true color scanning on the user's oral cavity to obtain a spatial arrangement of the user's teeth and a three-dimensional true color curved surface image of the user's teeth, wherein the spatial arrangement comprises relationships between the teeth and an occlusal relationship between a maxillary dentition and mandibular a dentition in an occlusal state.

14. The tooth virtual editing device of claim 13, wherein the image pattern recognition device performs pattern recognition on the three-dimensional image data of the user's oral cavity according to image information stored in the three-dimensional image basic database and determines a serial number of an object to which the three-dimensional image data belongs; and the virtual editing device indexes the serial number of the object to a specific object so as to obtain the image information of the object and retrieve editing item list information of the object in the three-dimensional image basic database.

15. The tooth virtual editing device of claim 13, wherein the system further comprises a cloud server connected with both the image pattern recognition device and the three-dimensional image basic database, and when the recognition for the image data send by the image acquisition device cannot be achieved by the image pattern recognition device, the image data is sent to the cloud server for artificial recognition to input the annotation information and revise the editing item list information, and then the three-dimensional image basic database is updated according to the recognition result, the annotation information and the editing item list information; and the cloud server performs iterative training on the image pattern recognition device based on the updated three-dimensional image basic database.

16. A computer device comprising a memory and one or more processors, the memory having stored therein computer readable instructions which, when executed by the one or more processors, the one or more processors perform the method of claim 1.

17. A non-transitory computer-readable storage medium having stored therein computer-readable instructions that, when executed by one or more processors, the one or more processors perform the method of claim 1.

* * * * *